United States Patent [19]
Marlin et al.

[11] Patent Number: 4,665,211
[45] Date of Patent: May 12, 1987

[54] PROCESS FOR PREPARING BIS(DIALKYLPHENYL) PENTAERYTHRITOL DIPHOSPHITES

[75] Inventors: Gary V. Marlin; James F. York, both of Morgantown, W. Va.

[73] Assignee: Borg-Warner Chemicals, Inc., Parkersburg, W. Va.

[21] Appl. No.: 804,037

[22] Filed: Dec. 3, 1985

[51] Int. Cl.$^4$ ................................................. C07F 9/15
[52] U.S. Cl. ...................................... 558/78; 558/118
[58] Field of Search ................................... 558/78, 118

[56] References Cited

U.S. PATENT DOCUMENTS

| | | | |
|---|---|---|---|
| 2,961,454 | 11/1960 | Gould et al. | 558/78 |
| 3,047,608 | 7/1962 | Friedman et al. | 558/118 |
| 3,205,250 | 9/1965 | Hechenbleikner | 558/78 |
| 3,787,537 | 8/1971 | De Marcq | 260/954 |
| 4,209,976 | 9/1981 | Hechenbleikner et al. | 558/78 |
| 4,305,866 | 12/1981 | York et al. | 260/45.7 PH |

FOREIGN PATENT DOCUMENTS 1180398  8/1967  United Kingdom .

Primary Examiner—Anton H. Sutto
Attorney, Agent, or Firm—Emily A. Richeson; Richard J. Schlott

[57] ABSTRACT

An improved transesterification process for preparing bis-(2,4-dialkylphenyl) pentaerythritol phosphates using n-alkanes or cycloalkanes as solvents to provide high spiro/cage isomer ratios.

5 Claims, No Drawings

PROCESS FOR PREPARING BIS(DIALKYLPHENYL) PENTAERYTHRITOL DIPHOSPHITES

BACKGROUND OF THE INVENTION

This invention relates to a method for preparing phosphite stabilizers and more particularly to a method for preparing bis-(dialkyphenyl) pentaerythritol diphosphites. Still more particularly, this invention relates to a process for preparing a mixture of bis-(2,4-di-t-butylphenyl) pentaerythritol diphosphite isomers having a high proportion of spiro isomer.

A great number of organo-phosphite stabilizers are known in the art and several general methods are available for their preparation. Widely used for this purpose are ester interchange reactions such as those disclosed for example in U.S. Pat. Nos. 2,961,454, 3,047,608, 3,204,250 and 3,787,537. The preparation of di-(2,4-di-t-butylphenyl) pentaerythritol diphosphite from a dialkyl or diaryl pentaerythritol diphosphite and a slight excess of 2,4-di-t-butylphenol by an ester interchange process is disclosed in U.S. Pat. No. 4,305,866. As is now well known in the art, and is set forth in the latter patent, pentaerythritol diphosphites produced by these processes are generally mixtures of the spiro and cage isomer, viz.

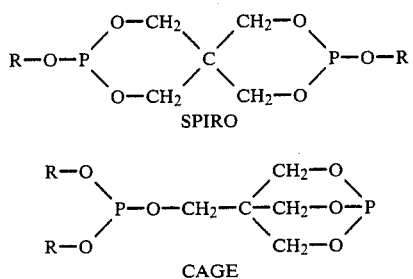

The proportion of the two isomers in the product mixture varies both with the method of preparation and with the nature of R. Transesterification processes usually provide spiro/cage ratios near 1/1 where R=alkyl, while ratios of 3/1 are more commonly produced where R=aryl. There is also some suggestion in the art, as is set forth in U.S. Pat. No. 4,290,976, that the spiro and cage isomers will be inter-converted at temperatures above about 75° C. where R=alkyl, increasing the proportion of cage isomer.

The proportion of spiro and cage structures in the product mixture significantly affects the physical characteristics of the product. As is well known, pure compounds exhibit sharp melting points, while mixtures exhibit broad and usually depressed melting ranges. For most pentaerythritol diphosphites, the spiro isomer has a significantly higher melting point than the cage isomer. Increasing the proportion of spiro isomer tends therefore to raise the melting range temperature of the mixture which reduces the tendency toward having waxy, low softening temperature characteristics. Even more beneficial are methods for isolating the spiro isomer in a pure or nearly pure form, such as by selective recrystallization from a suitable solvent. Selective recrystallization, however, may result in a substantial reduction in overall yield if the cage isomer constitutes a major fraction of the mixture, thereby markedly increasing the cost of manufacture.

An economically more favorable and therefore more desirable process would be one in which the spiro isomer is the predominant product. Such a process, particularly when coupled with a selective crystallization step, could provide good quality spiro isomer in greater yields, and thus have a significant manufacturing cost advantage.

SUMMARY OF THE INVENTION

This invention is a process for producing bis-(2,4-di-t-butylphenyl) pentaerythritol diphosphite as a mixture of the spiro and cage isomers having a high level of the spiro isomer. The process is a conventional transesterification process, the improvement in spiro isomer content resulting from the use of a normal alkane or cycloalkane as the reaction solvent. The ratio of spiro isomer to cage isomer in the product of this process will be greater than 6/1, and may be further increased by subsequent recrystallization.

DETAILED DESCRIPTION OF THE INVENTION

The process of this invention is a transesterification process wherein a mixture comprising a dialkyl or diaryl pentaerythritol diphosphite and 2,4-di-t-butyl phenol is heated under transesterification conditions to produce bis-(2,4-di-t-butylphenyl) pentaerythritol diphosphite. The displaced alkyl alcohol or phenol is removed from the reaction mixture during the course of the reaction by distillation. As is disclosed in U.S. Pat. No. 4,305,866, the pentaerythritol diphosphites which are preferred for use as the starting material for the purposes of the prior art transesterification process are diphenyl pentaerythritol diphosphite and dimethyl pentaerythritol diphosphite. The reaction mixture may employ a stoichiometric quantity of 2,4-di-t-butyl phenol, or a slight to moderate excess, on the order of 2.1 to about 2.5 or 3.0 moles of 2,4-di-t-butyl phenol per mole of the pentaerythritol diphosphite, may be employed to favor completion of the reaction.

The transesterification reaction will preferably be carried out in the presence of an alkaline catalyst. The alkaline catalyst preferably is an alkaline inorganic compound and most preferably is an alkali or alkaline earth metal oxide, hydroxide, carbonate or alcoholate, all of which are catalysts well known in the art as being useful for these purposes. The alkaline catalyst will be employed in minor amounts, normally from about 0.1 to 5 wt % of the reaction mixture.

An alternative transesterification process which also may be used in the preparation of bis(2,4-di-t-butylphenyl) pentaerythritol diphosphite is that disclosed in U.K. Pat. No. 1,180,398. In this alternative process a mixture of 2 moles of triphenyl phosphite, 2 moles of 2,4-di-t-butyl phenol and 1 mole of pentaerythritol are heated in the presence of an alkaline catalyst with the distillation of phenol. Such transesterification processes for the preparation of pentaerythritol diphosphites are well known and described in the art. Other reaction conditions, as well as variations in starting materials and particular catalysts are well known in the art, and such variations may be utilized in the practice of the improved process of this invention.

The process improvement which represents an advance over the processes of the prior art is the use of a particular solvent to attain a high spiro/cage isomer ratio in the product. The solvents useful in the instant process are normal or cyclic parafins having a boiling temperature above about 150° C., and preferably above about 200° C., at normal atmospheric pressure. More particularly, the solvent will be a saturated normal or cyclic hydrocarbon or hydrocarbon mixture having a solidification or freezing point below about 15° C. and a boiling point at atmospheric pressure above about 150° C. As a practical matter, in as much as the transesterification process proceeds with the distilling of phenol from the reaction mixture, the preferred solvent will have a boiling point above that of phenol, i.e. above about 200° C. Where the solvent boiling point is at or below that of the phenol, co-distillation of the solvent requires that make-up solvent be added to the reaction mixture continually, and such solvents are therefore not preferred. Still more particularly, the solvent will be a saturated hydrocarbon or mixture of saturated hydrocarbons selected from the group consisting of $C_{10}$–$C_{16}$ n-alkanes and $C_{10}$–$C_{16}$ cyclo-alkanes. Representative examples of suitable hydrocarbons are n-decane, n-dodecane, n-tridecane, n-hexadecane and the like, and the cyclic and polycyclic analogs thereof such as cyclododecane, bicyclo[4,4,0]decane(decahydronaphthalene) and the like. A variety of commercially available mixtures of n-alkane hydrocarbons are known which are substantially free of, or contain only minor amounts of branched parafins, and these mixtures may be employed as solvents for the purpose of this invention. The amount of solvent employed in the process of this invention will be determined primarily based on considerations of economics and practical handling. Where the solvent level in the product mixture is very high, i.e. well above about 65 to 70 wt %, the product losses due to solubility even at reduced temperatures become large and therefore economically impractical. At low solvent contents, below about 35 to 40 wt %, the resulting product mixture tends to solidify on cooling, making further handling difficult. As a purely practical matter, the amount of solvent to be added to the reaction mixture will thus lie in the range of from about 40 to about 70 wt % based on the (theoretical) product mixture.

The process of this invention will be better understood by consideration of the following examples, which are offered by way of illustration of the invention and not in limitation thereof.

EXAMPLES

In the following examples, designed to demonstrate the effect of various solvents on the spiro/cage ratio, a mixture of 380 g (1.0 mole) of diphenyl pentaerythritol diphosphite, 564 g (2.73 moles) 2,4-di-t-butyl phenol, 600 g of the solvent and 2.7 g of sodium methylate was prepared and placed in a sealed reaction vessel fitted with a stirrer, a vacuum fractionation column and a distillation receiver. The mixture was heated to 110°–130° C. under reduced pressure (10–20 mm) and held with stirring. Phenol was continually removed by distillation as the transesterification proceeded until substantially the theoretical amount of phenol was removed. The reaction mixture was cooled and analyzed by high pressure liquid chromotography to determine the spiro/cage ratio in the product.

The spiro/cage ratio for the products of the reaction conducted in a variety of solvents is summarized in Table I.

Examples 1–4 are representative of the process of this invention, while Control Examples A–E are provided for comparison purposes.

TABLE I

| EX. NO. | SOLVENT | SPIRO/CAGE | % (3) |
|---|---|---|---|
| 1 | n-decane | 18/1 | 77 |
| 2 | $C_{10}$–$C_{13}$ Parafin | 12.5/1 | 82 |
| 3 | $C_{12}$–$C_{14}$ Parafin | 7/1 | 80 |
| 4 | decalin | 12/1 | 81 |
| A | Branched Hydrocarbon | 2/1 | 74 |
| B | tetraglyme | 3.5/1 | 72 |
| C | isobutyl heptyl ketone | 6/1 | 72 |
| D | o-dichloro benzene | 10/1 | 80 |
| E | none (2) | 4/1 | 74 |

Notes
(1) $C_{10}$–$C_{13}$ parafin = mixed n-alkanes obtained as Norpar 12 from Exxon Company; $C_{12}$–$C_{14}$ Parafin = mixed n-alkanes, obtained as Norpar 13 from Exxon Company, tetraglyme = tetraethylene glycol, dimethyl ether; branched hydrocarbon = 200°–250° C. boiling range branched parafinic hydrocarbon mixture, obtained as Isopar M from Exxon Company
(2) none = Reaction of Example was run without any solvent; see U.S. Pat. No. 4,305,866.
(3) Sum of spiro and cage product as % of total crude reaction solids.

It will be apparent from a consideration of the spiro/cage ratios for Examples 1–4 that a product having a high spiro/cage ratio is obtained by the process of this invention. Quite surprising is the effect of a branched parafin solvent, Example A, which provides a substantially reduced spiro/cage ratio, even when compared with the product of Example E, run without solvent as is conventionally practiced in the art. It is not at all obvious that such a difference in behavior would result. Other high boiling solvents suggested in the art for use in such transesterifications, including ketones (Example C) and ethers (Example B) also failed to significantly improve the spiro/cage ratio in the product mixture.

EXAMPLE 5

The process of the example was repeated, using $C_{10}$–$C_{12}$ hydrocarbon (Norpar 12). At the end of the reaction the hot solution was filtered to remove minor solid contaminants, then cooled to allow crystallization of the phosphite. The crystallized product was collected by filtration and vacuum dried at 100° C./10 mm to provide 399 g (67% yield) of phosphite. By HPLC analysis, the product was 98.5 wt % spiro product.

Example 5 demonstrates the feasibility of producing substantially pure spiro phosphite by combining the improved process of this invention with a subsquent crystallization step from the same solvent.

Other solvents such as aliphatic ketones (control Example C) and o-dichlorobenzene (control Example D) may also increase the spiro/cage ratio above that of process run without solvent (control Example E). However, such solvents will not be suitable for the practice of this invention. Phosphites are quite soluble in such solvents and thus the product can best be recovered in adequate yield only by distillation or evaporation of the solvent, giving a crude product requiring further purification to remove by product compounds and reactants. This substantially reduces or eliminates any economic benefit over conventional processes run without solvent, even though the spiro/cage ratio is improved.

COMPARATIVE EXAMPLE F

The process of Example 3 was repeated, using Norpar 13 ($C_{12}$–$C_{14}$) parafin as the solvent and p-t-amylphenol in place of 2,4-di-t-butylphenol) to prepare bis(2-t-amylphenyl) pentaerythritol diphosphite. The crude product, analyzed as before, had a spiro/cage ratio of 1.51. This product, when prepared without using a solvent, had a spiro/cage ratio of 1.23.

COMPARATIVE EXAMPLE G

Three preparations of distearyl pentaerythritol diphosphite were made using stearyl alcohol as the alcohol reactant. The first, using Norpar 13 as the solvent, provided a product having sprio/cage ratio of 2.54. The product of the second preparation, made using Isopar M branched parafin as the solvent, had a spiro/cage of 1.56. When prepared without solvent, the spiro/cage ratio of the product was 1.34.

It is thus clear from these further Comparative examples that the process of this invention is limited to use in preparing bis(2,4-dialkylphenyl) pentaerythritol phosphites. It is quite surprising and clearly unobvious that the use of normal parafins as solvents in the preparation of bis-monoalkylphenyl (Comparative Example F) and bis-dialkyl (Comparative Example G) analogs will have very little effect on the spiro/cage ratio.

The process of this invention is thus an improved process for the preparation of bis(2,4-di-t-butylphenyl) pentaerythritol diphosphite wherein a conventional transesterification process is carried out in a liquid parafin or cycloparafinic hydrocarbon having a boiling temperature above about 150°, and preferably above about 200° C. Further refinements and modifications in the process will be apparent to those skilled in the art, and may be practiced without departing from the spirit and scope of the invention, which is defined by the appended claims.

We claim:

1. In a process for the preparation of bis(2,4-di-t-butylphenyl) pentaerythritol diphosphites wherein a reaction mixture comprising a bis-diester of pentaerythritol diphosphite and a 2,4-di-t-butylphenol in a molar ratio of from 1:2 to 1:3, is heated in the presence of an alkaline catalyst to effect a transesterification of said 2,4-dialkylphenol and wherein the transesterification byproducts are removed from the reaction mixture by distillation, the improvement wherein said reaction mixture includes a solvent having a boiling point above about 150° C., said solvent being selected from the group consisting of $C_{10}$–$C_{16}$ n-alkanes and $C_{10}$–$C_{16}$ cycloalkanes.

2. The process of claim 1 wherein said bis-diester of pentaerythritol is bis-diphenyl pentaerythritol diphosphite.

3. In an alkaline-catalyzed transesterification process for preparing bis(2,4-di-t-butylphenyl) pentaerythritol diphosphites, the improvement wherein the process is carried out in a saturated normal or cyclic hydrocarbon having a solidification point below about 15° C. and a boiling temperature above about 150° C.

4. The process of claim 3 wherein the hydrocarbon is selected from the group consisting of $C_{10}$–$C_{16}$ n-alkanes and $C_{10}$–$C_{16}$ cycloalkanes.

5. The process of claim 3 wherein the hydrocarbon is a mixture of n-alkanes selected from the group consisting of $C_{10}$–$C_{16}$ n-alkanes.

* * * * *